US005444030A

United States Patent [19]

Böttcher et al.

[11] Patent Number: 5,444,030
[45] Date of Patent: Aug. 22, 1995

[54] METAL COMPLEXES WITH A HIGH COORDINATION NUMBER

[75] Inventors: Axel Böttcher, Wesel; Manfred Döring, Jena; Jürgen Zehrfeld, Voerde, all of Germany

[73] Assignee: Rutgerswerke Aktiengesellschaft AG, Germany

[21] Appl. No.: 119,031

[22] Filed: Sep. 9, 1993

[30] Foreign Application Priority Data

Sep. 22, 1992 [DE] Germany ............ 42 31 680.4

[51] Int. Cl.$^6$ .............................. B01J 31/00
[52] U.S. Cl. ............................ 502/150; 502/151; 502/152; 502/167
[58] Field of Search ........... 502/152, 151, 150, 167

[56] References Cited

U.S. PATENT DOCUMENTS 4,105,667 8/1978 Thom .
4,193,893 3/1980 Count et al. ............... 502/151

OTHER PUBLICATIONS

Copy of European Search Report (2 pages).
Copy of J. Chem. Soc. (A) 1968 pp. 128–132.
Copy of J. Chem. Soc. (A) 1967 pp. 757–762.

*Primary Examiner*—Asok Pal
*Attorney, Agent, or Firm*—Bierman and Muserlian

[57] ABSTRACT

A process for the preparation of complex salts with additional coordinated ligands comprising reacting with through mixing at 20° to 200° C. a complex-forming metal salt of a metal of the second and third main groups of the Periodic Table and the subgroups thereof with a stoichiometric amount of at least one member of the group consisting of a chelating ligand and a Lewis base in the absence of a solvent according to the equation:

$$M_m{}^{a+}(SR^{b-})n + xL \cdot cH + yB^- \rightarrow m[M^{a+}(SR^{b-})(n-o)L_xB_y] + o \cdot SR^{b-} + c \cdot H^+ \qquad I$$

wherein M is a metal ion, SR is an acid radical of an organic or inorganic acid, B is a Lewis base, and L is a chelating ligand, $m \cdot a = b \cdot (n-o) + c \cdot x$, wherein $a=$ an integer of 1–8, $b=$ an integer of 1–3, $c=$ an integer of 0–4, $m=$ an integer of 1–3, $n=$ an integer of 1–8, $o=$ an integer of 0–8, $x=$ an integer of 0–4, $y=$ and integer of 1–16, wherein $(n-o)+x+y \leq 16$ and the complex salts formed thereby useful as latent curing catalysts.

10 Claims, 9 Drawing Sheets

METAL COMPLEXES WITH A HIGH COORDINATION NUMBER

A multiplicity of different organo-metallic complex compounds are known which are used as catalysts, accelerators, initiators and the like for organic reactions. In recent times, chelate complexes of the transition metals with diketones, dithocarbamide acid derivatives, dihydroxy compounds, diamines or other difunctional ligands have especially gained importance as catalysts for polymerization and curing reactions. The production of such simple neutral transition complexes is described for example in U.S. Pat. Nos. 4,337,210, 4,338,254, 4,008,260 or 4,279,829.

Neutral transition complexes in which ligands of different types are coordinated around a central atom have been produced in complicated processes, wherein dry, solvent-free transition metal complexes produced in a first step are coordinated in a second process step with additional ligands such as pyridine, butylamine or benzylamine (Olszewski, et al; J. Inorg. Nucl. Chem., Vol 27, p 1043–1048 (1965).

Processes have also been described by which mixed coordinated complexes of this type can be produced in a single-step process, but for carrying them out, expensive transition metal acetates are required. In addition, yields fluctuate highly between 20 and 88% so that carrying out the process on a commercial scale has proven to be uneconomical (Bereman, et al, Inorg. Chim. Acta, Vol. 130, p 195–201 (1987).

Also known is a single-step process from DD-A5-292 463. However, in this process, the reaction must take place in expensive organic solvents or mixtures in the presence of organic auxiliary bases such as tributylamine or other tertiary amines. In this process, the effect of the solution behavior of the complexes formed is of disadvantage. Since the neutral complexes are partially soluble in the solvents used, losses in terms of yield must be accepted which cannot be compensated by concentrating the solutions. The accumulating amounts of impure solvents must also be disposed of or must be reprocessed. The same applies for the organic ammonium salts generated as by product. It is also a disadvantage of this process that precisely these ammonium salts which are partially odor-intensive adhere in small quantities to the end product and require an additional purification process.

Not only is the production of previously known organo-metallic complex compounds afflicted with shortcomings, but also in their use as polymerization or curing catalysts for the production of high-quality products, problems occur which until now could only be reasonably solved by the addition of further additives or by a complicated and time-intensive temperature and pressure guidance. If, for example, the addition products of U.S. Pat. No. 4,487,914 comprising imidazole or substituted imidazoles, an epoxy compound and a metal salt, are used as curing catalysts for epoxy resins, extremely strong temperature increases occur during the curing reaction which lead to the discoloration of the products and to inhomogeneities in the cured material.

The addition of solvents to decrease the high reactivity after the onset of the polymerization reaction, as described in DE-OS 28 10 428, also does not lead to a satisfactory solution since the later removal makes necessary additional processing steps and the cured products show undesirable hollow spaces which increase the capability for absorbing water or affect negatively the resistance to reagents and impair significantly the electrical and mechanical properties of the polymer.

The imidazole metal complexes of U.S. Pat. Nos. 3,638,007, 3,792,016 and 4,101,514 and DE 23 00 489 as latent curing agents become only active at temperatures above 170° C. and split off imidazole, and thereby cause reduced product qualities through undesirable side reactions. It is possible to produce with the neutral metal complexes known from PCT/WO/00419, polymer mixtures which are stable at room temperature and during storage, which, however, already cure to high-quality products at temperatures above 50° C. However, the disadvantage of these catalysts is that after the onset of the reaction, complete curing takes place directly. A stepwise curing which would for example permit the production of storage stable prepregs utilizing only one single curing system, is not possible.

OBJECTS OF THE INVENTION

It is an object of the invention to provide an environmentally safe and economical process for the preparation of transition metal complexes from inexpensive metal salts in a one step process in substantially quantitative yields.

It is another object of the invention to provide novel transition metal complexes with additional coordinated ligands of high purity without expensive purification and drying steps.

It is a further object of the invention to provide polymer mixtures which are storage-stable containing as the sole curing catalyst a transition metal complex which mixtures are precurable at slightly increased temperatures to form intermediate products capable of being fully cured at increased temperatures after being formed.

These and other objects and advantages of the invention will become obvious from the following detailed description.

THE INVENTION

The novel process of the invention for the preparation of complex salts with additional coordinated ligands comprises reacting with through mixing at 20° to 200° C. a complex-forming metal salt of metal of the second and third main groups of the Periodic Table and the subgroups thereof with a stoichiometric amount of at least one member of the group consisting of a chelating ligand and a Lewis base in the absence of a solvent according to the equation:

$$M_m^{a+}(SR^{b-})_n + xL\cdot cH + yB^{31} \rightarrow m\,[M^{a+}(SR^{b-})_{(n-o)}L_xB_y] + o\cdot SR^{b-} + c\cdot H^+ \qquad \text{I}$$

wherein M is a metal ion, SR is an acid radical of an organic or inorganic acid, B is a Lewis base, and L is a chelating ligand, $m\cdot a = b\cdot(n-o) + c\cdot x$, wherein $a$ = an integer of 1–8, $b$ = an integer of 1–3, $c$ = an integer of 0–4, $m$ = an integer of 1–3, $n$ = an integer of 1–8, $o$ = an integer of 0–8, $x$ = an integer of 0–4, $y$ = an integer of 1–16, wherein $(n-o)+x+y \leq 16$ and the complex salts formed thereby.

The neutral complexes produced can be used as sole curing catalysts for storage-stable prepregs, for epoxy resins and their mixtures, and for the production of ductile and postforming, precured epoxy resins, for adhesive substances as well as polyurethanes and their mixtures with other resins.

It has now been found that organic compounds acting as Lewis bases can be bound in high numbers in the first and second coordination sphere as ligands around a central metal atom if they are heated together with a suitable metal salt or metal complex without solvent and with intensive mixing, and specifically at least up to and above the melting temperature of the ligand. If these Lewis bases are liquids, the reaction can take place at room temperature, i.e. the metal salt does not need to be melted. Overall, the composition of the resulting complexes can be determined solely through the stoichiometric ratio of the components used.

As investigations have shown, as a function of the temperature set in the melt and the quantities of Lewis base and metal salt or complex used, new complexes with more than eight ligands can be obtained. The coordinated ligands of such a complex can all be identical, but coordinated complexes can also be obtained. Identical educts therein lead under identical reaction conditions nearly quantitatively and reproducibly to identical end products.

Without further processing, surprisingly the complexes obtained can be used as sole curing catalysts for polymer mixtures for the production of precured products wherein the precuring is brought about at low temperatures as well as also the postcuring after the forming through this catalyst.

While the precipitation of the complex salts customarily takes place only after a given waiting period, the complexes formed can be obtained directly from the reaction mixture as fine-grained powder. This is achieved through very slow cooling at high mixing speed, by grinding the cooled reaction product, by spraying or by other methods of disintegration.

If acid, which is potentially released as a byproduct and still adhering, interferes, it can be removed in a simple manner by washing with a suitable solvent in which the complex is insoluble. Due to the simple synthesis, the complexes can be obtained batchwise as well as also continuously.

The process has the particular advantage that reproducible, uniform, odorless complexes with additionally coordinated ligands are obtained in high yields, which when used as curing accelerators can be readily apportioned even after relatively long storage times, can be distributed and dissolved uniformly in the resin. Complexes produced up to now using amine auxiliary bases were obtained as unpleasantly smelling products which tend to cake together, which are contaminated by amine complexes which have also been formed and which can only be apportioned with difficulty after a moderately long storage time. Since the complexes of the invention are produced without the addition of solvents, the entire production process is more environmentally friendly and simultaneously more economical than previously known processes. Specifically, the total costs are not only decreased by the cost of the solvent but also those of solvent recycling, simpler reactor design and by costs which would normally need to be expended for special safety measures which must be taken in the presence of boiling solvents. Furthermore, the complexes are produced in significantly shorter reaction times which is linked to additional energy savings.

The potentially mixed coordinated metal complexes of the invention can be produced according to the following single-stage reaction wherein the reactants are used in stoichiometric quantities:

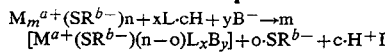

wherein M is a metal ion, SR is an acid radical of an organic or inorganic acid, B is a Lewis base, and L is a chelating ligand, $m \cdot a = b \cdot (n-o) + c \cdot x$, wherein $a$=an integer of 1–8, $b$=an integer of 1–3, $c$=an integer of 0–4, $m$=an integer of 1–3, $n$=an integer of 1–8, $o$=an integer of 0–8, $x$=an integer of 0–4, $y$=an integer of 1–16, preferably 9–12 and $(n-o)+x+y \leq 16$, or:

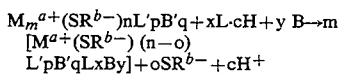

with M, SR, L, a, b, c, m, n, o, x and y defined as above, and $m \cdot a = (n-o) \cdot b + p + x \cdot c$ B′=a Lewis base, potentially identical with B and L′=a chelating ligand, potentially identical with L, $p$=an integer from 0 to 4, $q$=an integer from 0 to 8 and wherein $(n-o)+p+q+x+y \leq 16$.

As ligands, uncharged, simple Lewis bases with a free electron pair, multitoothed chelating agents, i.e. compounds which can occupy more than one coordination site on the central atom can be used. Ligands to be coordinated can be identical, already bound or different, and be present as a mixture in the reaction mixture.

As the metal ion ($M^{a+}$), any complexing metal ion can be used, but preferred are the ions of the second and third main group of the periodic system of elements as well as metal ions of the elements of the subgroups. Preferred metal ions are cobalt, nickel, iron, zinc or manganese ions which are used in the form of cost-effective metal salts for the production of the complexes of the invention.

Examples of metal salts are copper salts such as copper chloride, copper bromide, copper fluoride, copper nitrate, copper fluoroborate, copper sulfate, copper acetate, copper trifluoroacetate, copper stearate, copper octoate, copper methacrylate, copper malonate, copper benzoate; nickel salts such as nickel chloride, nickel fluoride, nickel sulfate, nickel fluoroborate, nickel tallate, nickel stearate or nickel salts of other organic acids, such as for example of ricinoleic acid; calcium salts such as calcium chloride, calcium bromide; cobalt salts such as cobalt chloride, cobalt fluoride, cobalt nitrate, cobalt sulfate, cobalt octoate, cobalt fluoroborate, cobalt stearate; zinc salts such as zinc bromide, zinc chromate, zinc chloride, zinc stearate, zinc octoate, zinc ethylhexoate; mercury salts such as mercury bromide or chloride, zirconium salts such as zirconium sulfate or zirconium chloride; indium salts such as indium fluoroborate; silver salts such as silver nitrate; chromium salts such as chromium chloride; manganese salts such as manganese chloride, manganese sulfate; tin salts such as tin chloride, cadmium salts such as cadmium chloride, iron salts such as iron chloride, titanium salts such as titanium chloride; vanadian salts such as vanadium chloride, antimony salts such as antimony chloride and the like. It is understood that the listed salts are only a small portion of the metal salts usable in the process. Preferred for the production of the curing catalysts of the invention are inexpensive inorganic salts. However, well suited are also salts of organic acids which have a pK value of approximately 1.2 to 5.7 (relative to a 0.1 N solution) and specifically for example those of acetic acid, oxalic acid, lactic acid, tartaric acid, malic acid, fumaric acid, malonic acid or of other suitable organic acids. Examples of acid radicals (SR) are all salts described above.

As chelating ligand L, all organic compounds in principle can be used which have at least two atom groupings with free electron pairs or electron gaps for forming complex compounds. Examples are dioximes, α- and β-hydroxycarbonyl compounds, hydroxycarboxylic acids, ketones, aldehydes and their analogs or enolizable 1,3-diketones. Preferred chelating ligands are acetylacetone, benzoylacetone and their homologs, dipivaloyl methane or dimethylglyoxime.

In the metal complex compounds, Lewis bases (B) or B' can all be nucleophilic molecules or ion which have a lonely electron pair. Examples are pyridine, pyrimidine or imidazole compounds, ethers, including cyclic ethers such as tetrahyrofuran, aliphatic and aromatic alcohols, ketones, thioethers or mercaptans. But Lewis bases in the complexes of formulae I and II can also be CH-acidic compounds which are present as Lewis bases, i.e., CH-acidic compounds in which a proton is split off. Examples of such CH-acidic Lewis bases are CH-acidic pyridines, malonic acid diester or dinitrile, acetoacetic acid ester, cyanoacetic acid ester or nitromethane.

The charge equalization of the metal cations of the metal complex compounds can take place through the ligands themselves as well as also through ionic Lewis bases. It is therein understood that the number of charge-carrying ligands is reduced if the complex comprises ionic Lewis bases. A further embodiment of the complexes of the invention resides in that the CH-acidic Lewis bases are bound through nitrogen and/or oxygen and/or sulfur and/or phosphorus atoms, or hydrogen bridges to the metal chelate compound.

For carrying out the reaction, the starting compounds in stoichiometric ratio relative to the desired end product are weighed, intensively mixed and heated to the reaction temperature. Depending on the aggregate state of the compounds used, the reaction takes place at temperatures between 20 and 200° C., preferably 25 to 150° C. If the ligands to be coordinated, whether Lewis bases or chelating ligands, are present in liquid form, the reaction temperature is lower than in a mixture of solid reaction partners. In any case, heating while mixing intensively must take place until a homogeneous melt is present. Then the reaction conditions are kept constant until the entire metal salt has reacted and the new complex is formed. The end of the reaction can be recognized by a change of the color, but it can also be determined on the basis of the reactivity by determining the B time in the reaction with a base epoxy resin.

It is also possible to determine the end analytically through, for example, the determination of metal value or measurement of the UV-VIS absorption. However, these methods are expensive and complicated and, therefore, are not viewed as being realistic for commercial production. The reaction product is obtained in the form of a fine-grained powder without further processing if very slow cooling takes place while high mixing speeds are maintained, the cooled product is finely ground, sprayed after the termination of the reaction or subjected to another method of disintegration.

If the complex is to be used for curing resins which react sensitively to possibly adhering compounds used or by-products formed, such as organic or inorganic acids, it can simply be washed with solvents. Suitable for this purpose are solvents in which the complexes themselves are insoluble such as water by which potentially non-converted metal salt is removed, alcohols such as ethanol, methanol, propanol or also dimethylformamide or other organic solvents through which possible excess ligand is washed out.

As a possible reaction vessel with appropriate internal fittings, continuously operated flow tube reactors of different implementations can be used which, in the simplest case, can be preceded by small mixing chambers as well as also a loop-type bubble column with forced circulation or simple stirred tank reactors with or without internal fittings, optionally connected in cascade. A special advantage of this continuous process is the possibility of being able to obtain a product which can be used without further processing as a polymerization or curing catalyst. This product is a fine-grained, pourable product which even after a relatively long storage time does not tend to cake together.

If complexes with especially high coordination number are to be produced, it is possible, after a first reaction time in which all reaction partners present in the solution have completed the reaction, to add further chelating ligands or further Lewis bases and to allow the reaction mixture again to react while mixing it well. In this way, the coordination number can be further increased. In other words, a further coordination sphere can be occupied in which customarily water molecules are bound in hydrate containing crystals. This can be carried out especially advantageously in a flow tube reactor with multiple feed possibilities.

Through the described process inter alia, the following complexes can be produced: hexa (imidazole) - cobalt (II) acetate, undeca (imidazole) - cobalt (II) sulfate, tetrakis (1-methylimidazole) - nickel (II) bromide, deca (imidazole) - nickel (II) chloride, hexa (imidazole) - magnesium bromide, bis (acetylacetonato) zinc (II) dipyridine, bis (dipivaloylmethanato) - iron (II) diimidazole and bis (octoate) - zinc (II) di(1-methylimidazole).

The complexes due to the fact that they are fine-grained, can be especially easily dissolved in the polymer mixtures based on epoxy resins or polyurethane resins to be cured and, after the onset of the curing reaction, lead to especially short curing times. The curing of the resins takes place at temperatures between 50 and 180° C., preferably 60 to 140° C.

Curing experiments with complex salts which have an especially high coordination number or with such salts in which the Lewis bases are bound in a second coordination sphere, show two curing stages, and particularly if low complex concentrations are used. This is of particular advantage since in this way, resin systems for the production of precured products can be made available whose pre- and post- curing can be brought about by only one single curing catalyst. In addition, through this possibility, an interaction between the previously used catalyst systems for precuring and postcuring is avoided so that, precisely for this reason, the new complex compounds are effective in low concentrations as catalyst for both curing stages of precured products.

The complex salts can be used in concentrations of 0.01 to 50 percent by weight, preferably 0.1 to 20 percent by weight, relative to the total resin mixture, for the curing of epoxy resin products as well as also of polyurethanes. All epoxy compounds with more than one epoxy bond can be cured through the catalysts of the invention. Preferred epoxy compounds are polyphenol glycidyl ethers, for example epoxidized novolaks for the reaction products from epichlorophydrin and bisphenol A or bisphenol F. Epoxy resins of this type have an epoxy equivalent of 160 to 500.

The above listed polyfunctional epoxy compounds (this expression includes also the term epoxy resin) can be precured and postcured or directly cured individually or in mixtures, optionally in the presence of solvents. But they can also be used in a mixture with monoepoxides (so-called reactive thinners). Equally well suited are glycidylized anilines such as diglycidyl aniline or 4,4,4',4-tetraglycidyl diamino diphenylmethane.

The catalysts of the invention are also suitable in the described manner as curing agents for all mixtures cross-linked to polyurethanes which comprises monomers, oligomers or prepolymers with free isocyanate groups. Corresponding mixtures are known from Kunststoff Handdbuch Vol. 7, Polyurethanes, Becker et al; Editor Dr. Gunter Oertel, Carl Hanser Verlag, 1983. Among these mixtures are also mixtures with other polymers such as polycarbonates, polyacrylates, unsaturated polyester resins, in particular, however, with polyepoxides.

Depending on the choice of the curing catalysts to be used after the addition of the catalysts, resins having stability in storage or resins precuring at low temperatures are obtained, which, after forming, cure at increased temperatures between 80 to 200° C., preferably 100 to 150° C., but are readily ductile and postforming in the precured state and can be stored for relatively long periods of time.

The curing behavior can be utilized to produce adhesion-free prepregs storable for relatively long periods of time which, after the final curing, have especially high product qualities since it is possible to work without solvents with the curing catalysts of the invention. In addition, they can very easily be mixed uniformly with the resin mixtures.

Figure 1:
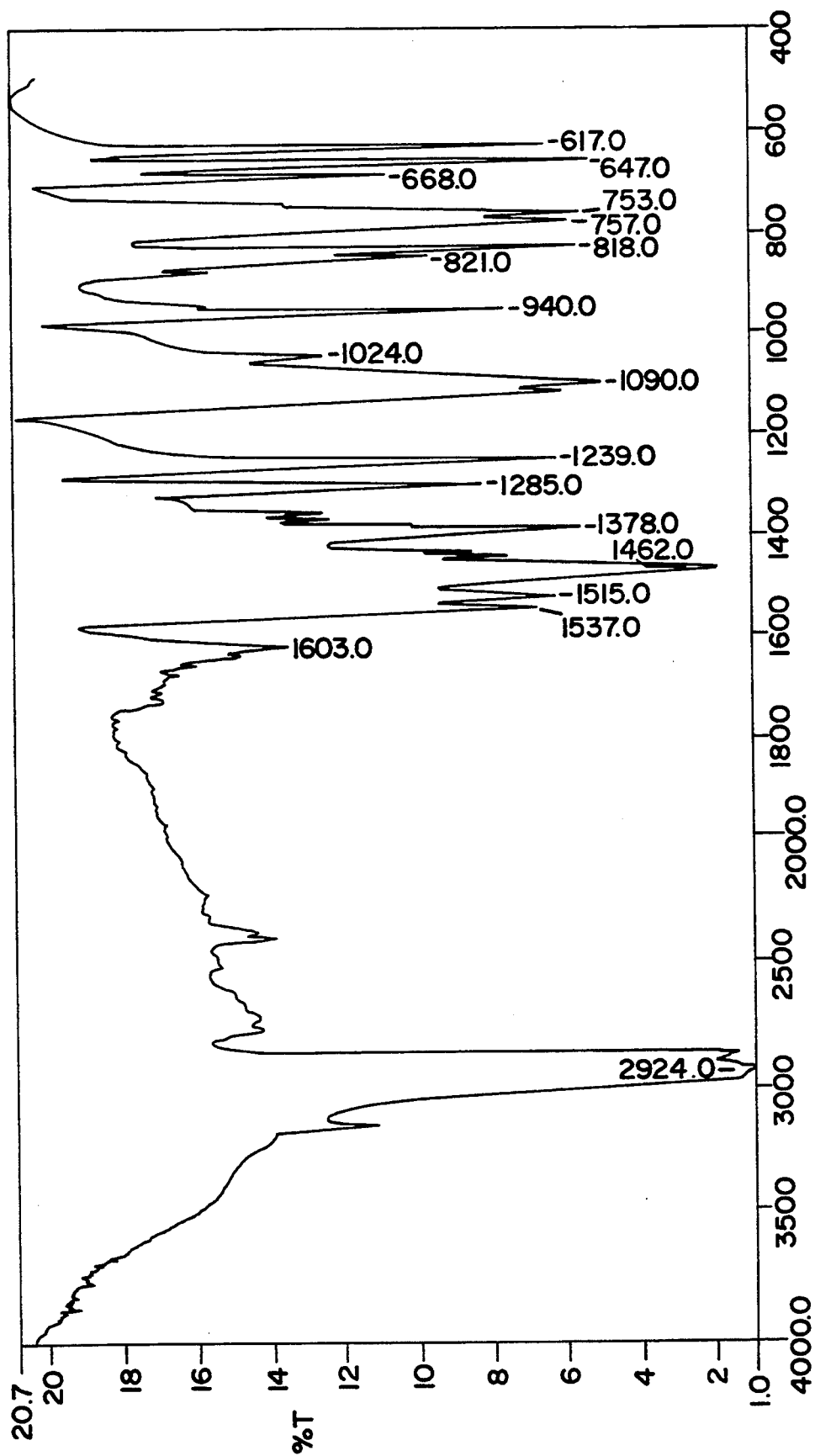
FIGS. 1 to 3 are IR spectra of the complexes of Examples 9 to 11.

In the following examples, there are described several preferred embodiments to illustrate the invention. However, it is to be understood that the invention is not intended to be limited to the specific embodiments.

EXAMPLE 1

One mole of nickel (II) chloride and 10 moles of imidazole were heated to their melting temperatures while stirring intensively at 200 to 400 rpm and the reaction was completed after 5 minutes maximum. The yield of deca(imidazole)-nickel (II) chloride was 98.5% based on the metal salt.

| | Analysis: | | | | |
|---|---|---|---|---|---|
| | Ni | C | H | N | Cl |
| Calculated: | 7.3% | 44.4% | 4.9% | 34.7% | 8.8% |
| Found: | 7.3 | 44.0 | 4.9 | 34.8 | 8.9 |

EXAMPLE 2

Using the procedure of Example 1, 1 mole of cupric sulfate and 4 moles of 2-methyl-imidazole were melted with vigorous stirring and after 5 to 10 minutes, the complex of tetra(2-methyl-imidazole)-cupric sulfate was formed with a 97.5% yield based on the metal salt.

| | Analysis: | | | | |
|---|---|---|---|---|---|
| | Cu | C | H | N | S |
| Calculated: | 13.0% | 39.4% | 4.9% | 23.0% | 6.6% |
| Found: | 13.0 | 39.8 | 5.0 | 22.9 | 6.4 |

EXAMPLE 3

A mixture of 1 mole of ferrous chloride and 6 moles of 1-methyl-imidazole were placed in a flow-tube reactor and after a brief reaction time at room temperature, the complex of hexa(1-methyl-imidazole)-ferrous chloride was formed with a 99% yield based on the metal salt.

| | Analysis: | | | | |
|---|---|---|---|---|---|
| | Fe | C | H | N | Cl |
| Calculated: | 9.0% | 46.8% | 5.2% | 27.1% | 11.5% |
| Found: | 9.0 | 46.8 | 5.5 | 27.2 | 11.5 |

EXAMPLE 4

1 mole of nickel (II) acetate and 6 moles of imidazole were heated to 100° C. in a stirred reactor with thorough mixing at 200 to 400 rpm for 5 to 10 minutes to obtain a complex of hexa (imidazole) nickel (II) acetate with a 97.5% yield, based on the metal salt.

| | Analysis: | | | |
|---|---|---|---|---|
| | Ni | C | H | N |
| Calculated: | 10.1% | 45.1% | 5.1% | 28.7% |
| Found: | 10.0 | 45.5 | 5.0 | 28.5 |

EXAMPLE 5

A thoroughly stirred mixture of 1 mole of cobalt (II) sulfate and 11 moles of imidazole was introduced into a flow tube reactor and heated at about 100° C. for 15 to 20 minutes to obtain the complex of deca(imidazole) cobalt (II) sulfate.

| | Analysis: | | | | |
|---|---|---|---|---|---|
| | Co | C | H | N | S |
| Calculated: | 6.5% | 43.9% | 4.9% | 34.1% | 3.5% |
| Found: | 6.5 | 48.5 | 5.0 | 34.0 | 3.3 |

EXAMPLE 6

1 mole of nickel (II) chloride hexahydrate, 2 moles of acetylacetone and 4 moles of pyridine were thoroughly mixed in a stirred reactor for 5 to 10 minutes to obtain the complex of bis (acetylacetonato)-nickel (II) dipyridine in a 96% yield, based on the metal salt. The pyridine chloride formed was removed by water washing.

| | Analysis: | | | |
|---|---|---|---|---|
| | % Ni | % C | % H | % N |
| Calculated: | 14.2 | 57.8 | 5.8 | 6.7 |
| Found: | 14.1 | 57.5 | 6.1 | 6.8 |

EXAMPLE 7

1 mole of cobalt (II) carbonate was thoroughly mixed with 2 moles of salicylaldehyde with an excess of 1-methyl imidazole at moderate temperatures using the procedure of Example 1 to obtain a 97% yield of bis-(salicylaldehyde)-cobalt (II) di(1-methylimidazole)

| | Analysis: | | | |
|---|---|---|---|---|
| | % Co | % C | % H | % N |
| Calculated: | 12.7 | 56.8 | 4.7 | 12.0 |
| Found: | 12.5 | 56.5 | 4.8 | 12.3 |

EXAMPLE 8

The production of prepreg material was effected by the known processes of wet technology or by the hot melt process. The catalyst was thoroughly mixed with diglycidyl ether of the bisphenol-A (Rütapox 0164). If the mixture was processed by wet technology, the solvent used was methyl ethyl ketone. The resin content of the prepreg after either of the processing methods was 50 percent by mass and the flow of resin is 30 percent by mass. The storage stability of the prepreg at room temperature compared to the pure Lewis base is shown in the following Table. (Storage stability is not given if the flow of the resin was <10 percent by mass.)

TABLE

| | Catalyst acc. to Example 1 | Imidazole | Comparison experiment hexa(imidazole)-Ni(II) Chloride |
|---|---|---|---|
| Wet technology | 45 days | 2 days | 6 days |
| Hot Melt | 43 days | 1 hour | 6 days |
| | Catalyst acc. to Example 2 | 2-methyl-imidazole | |
| Wet technology | 54 days | 4 days | |
| Hot Melt | 52 days | 3.5 hours | |
| | Example 3 | 1-methyl-imidazole | |
| Wet technology | 62 days | 5 days | |
| Hot Melt | 59 days | 5 hours | |

EXAMPLE 9

Into a stirred tank reactor, 1 mole of mercury -(II) chloride and 2 moles of 1-methylimidazole were heated to 100° C. while mixing vigorously at 200 to 400 rpm to obtain di-(1-methylimidazole)-mercury (II) chloride within 5 to 10 minutes in a yield of 97.5%.

EXAMPLE 10

Into a stirred tank reactor, 1 mole of aluminum (III) chloride and 3 moles of 1-methylimidazole were heated to 100° C. while stirring vigorously at 200 to 400 rpm to obtain di-(1-methyl-imidazole)-aluminum (III) chloride (II) within 5 to 10 minutes in a yield of 97%.

EXAMPLE 11

Into a stirred tank reactor, 1 mole of niobium (III) - chloride and 3 moles of 1-methyl-imidazole were heated to 100° C. while stirring vigorously at 200 to 400 rpm to obtain tri(1-methylimidazole)-niobium (III) chloride within 5 to 10 minutes in a yield of 98%.

Figure 2:
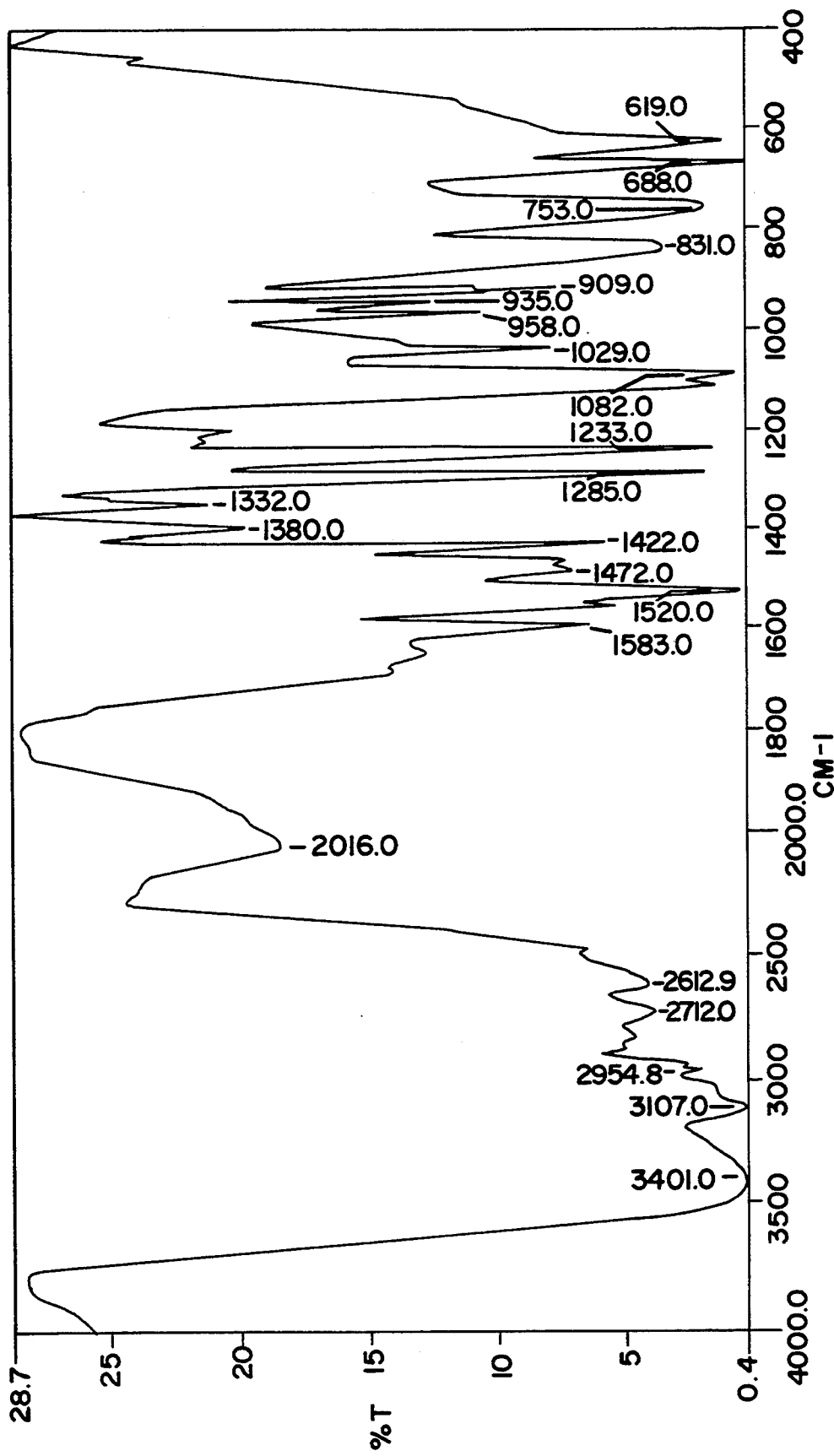
Figure 3:
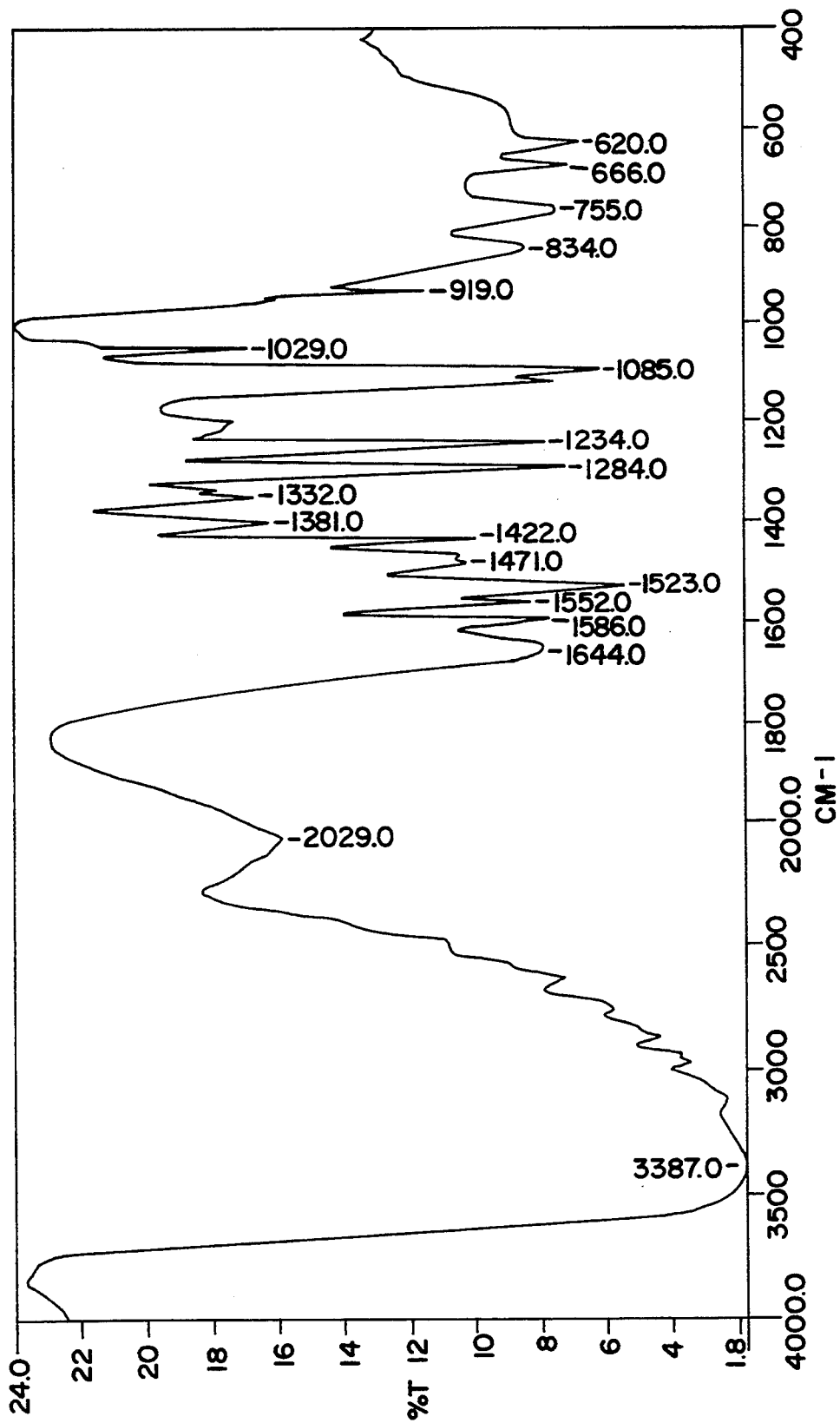
Figure 4:
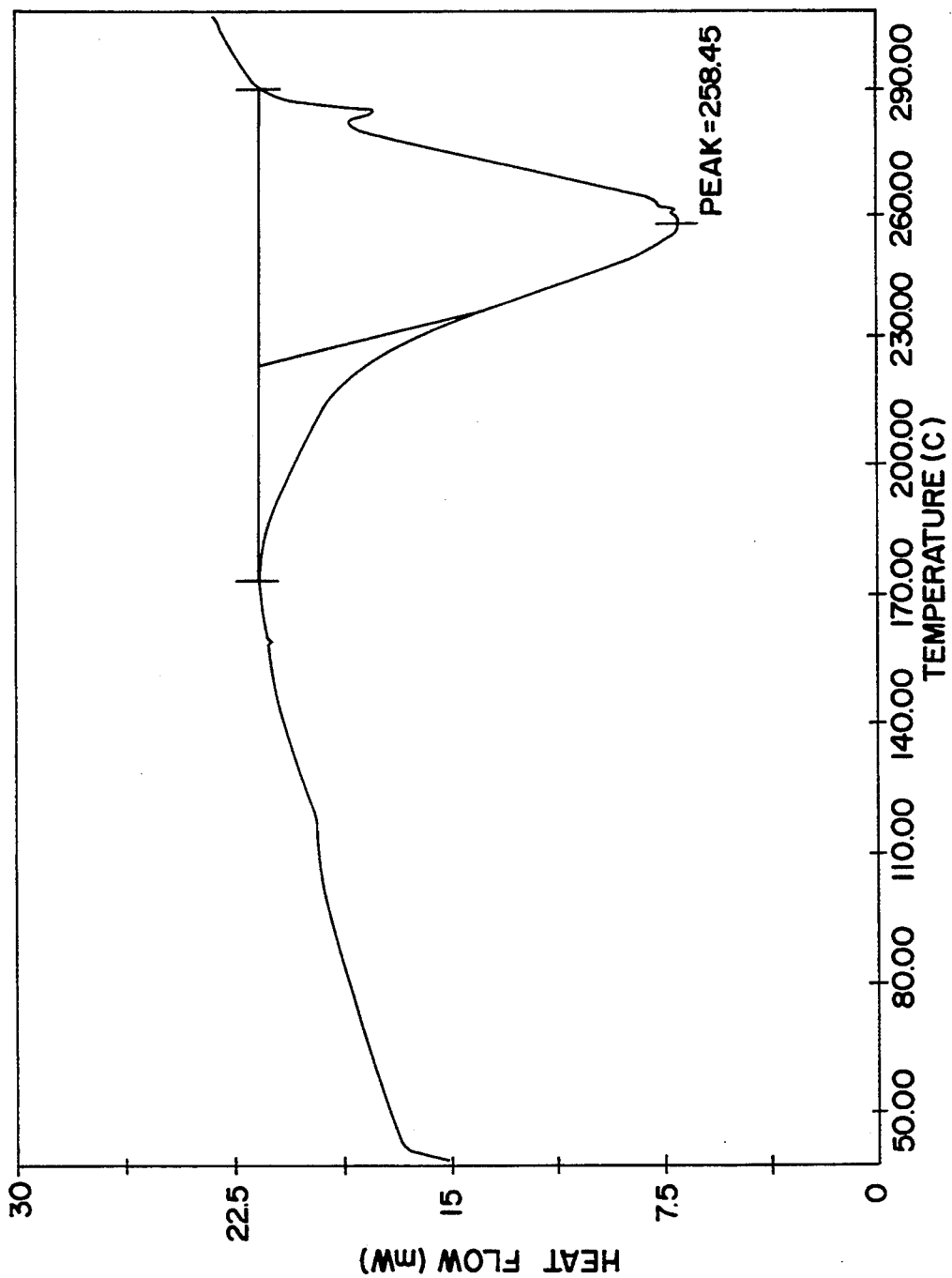
FIGS 4 to 9 are the corresponding dynamic and isothermic DSC diagrams of Examples 9 to 11.
Figure 5:
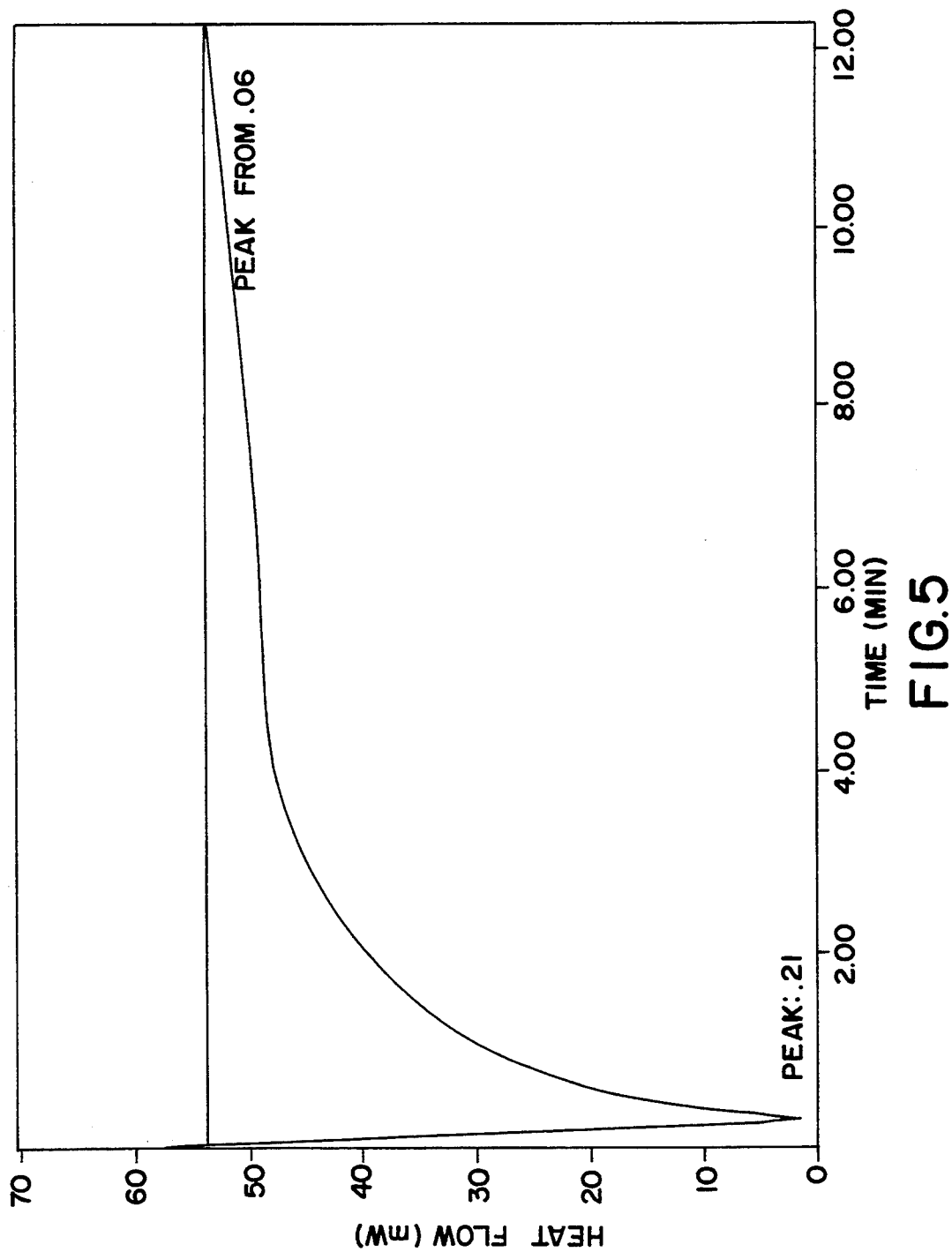
Figure 6:
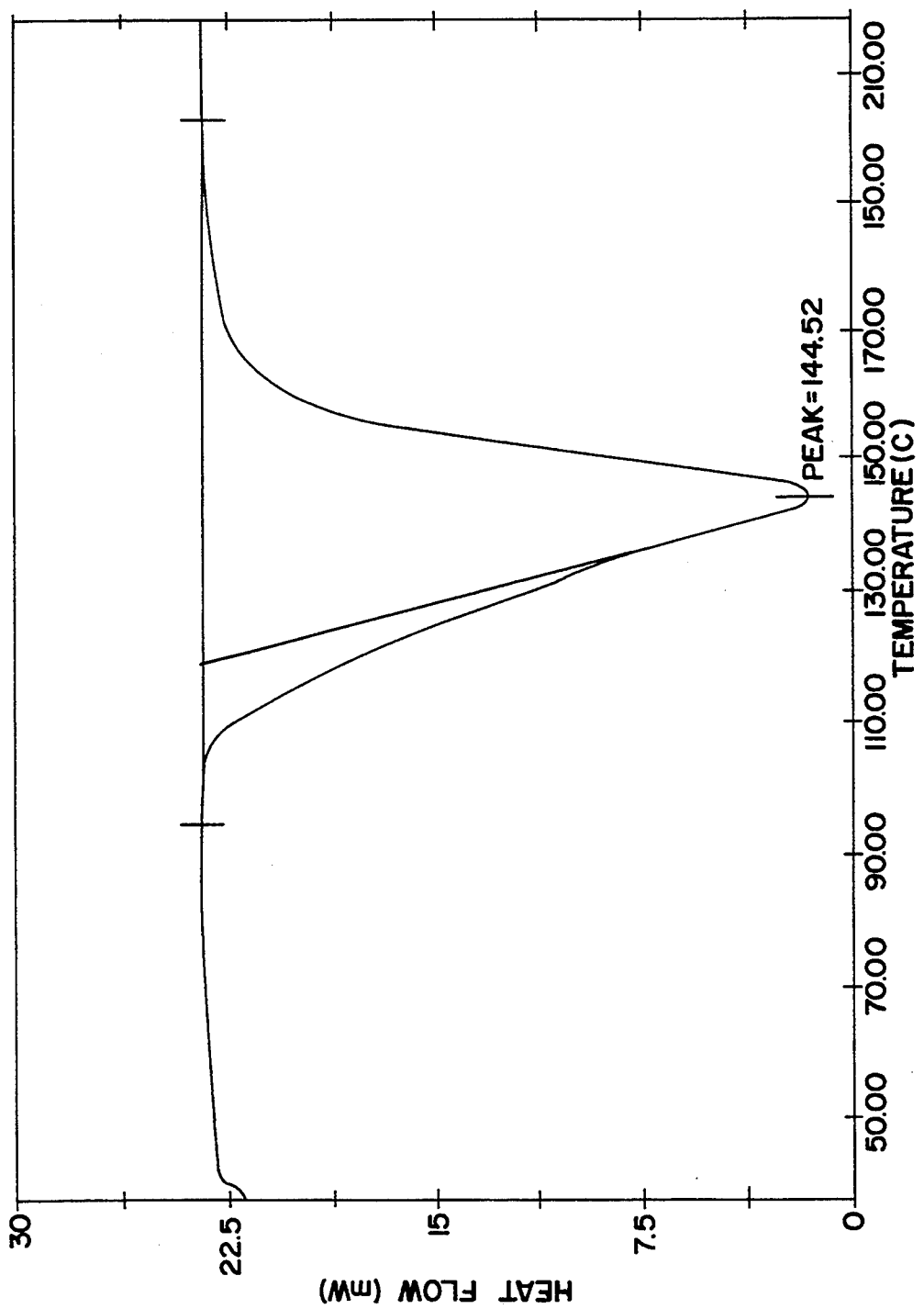
Figure 7:
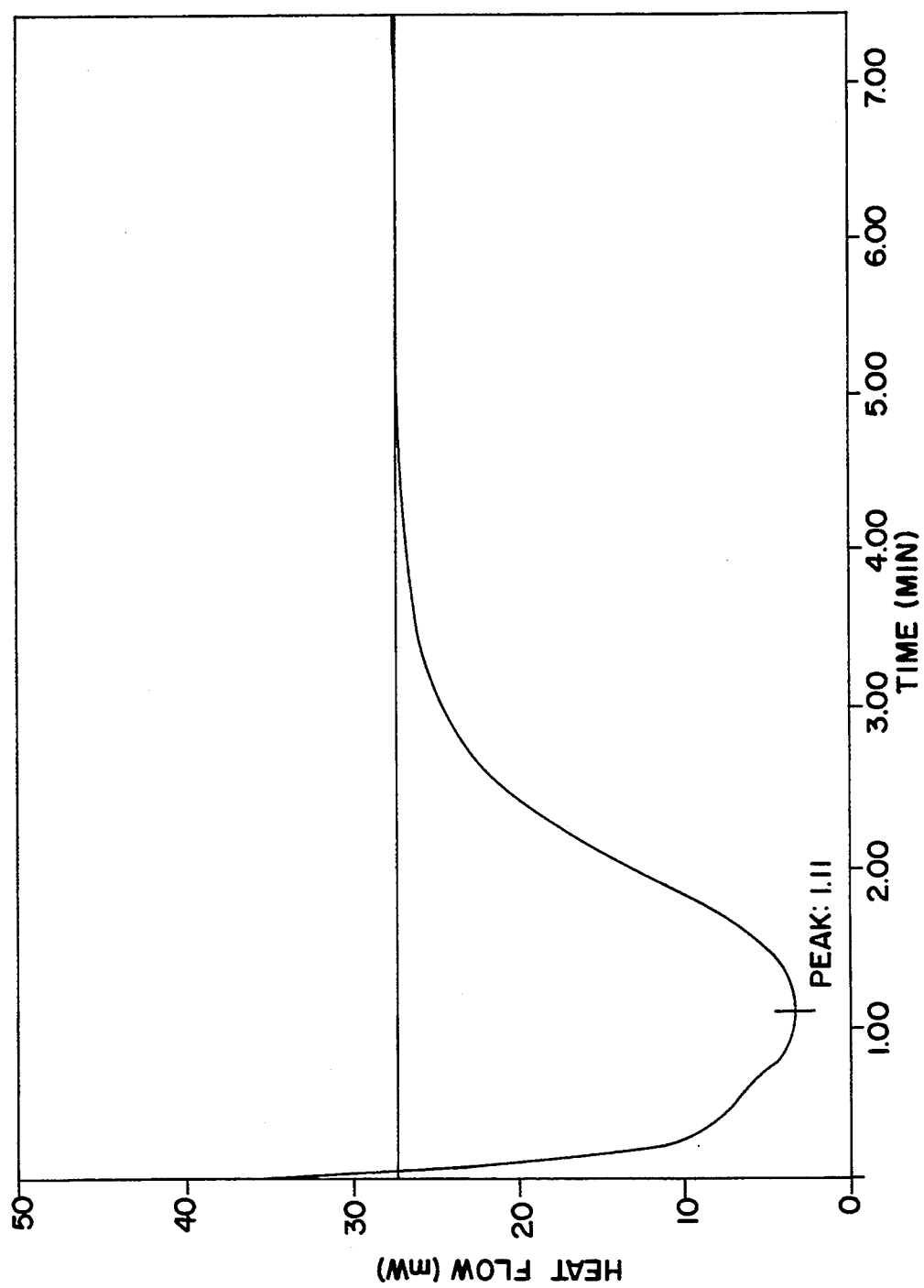
Figure 8:
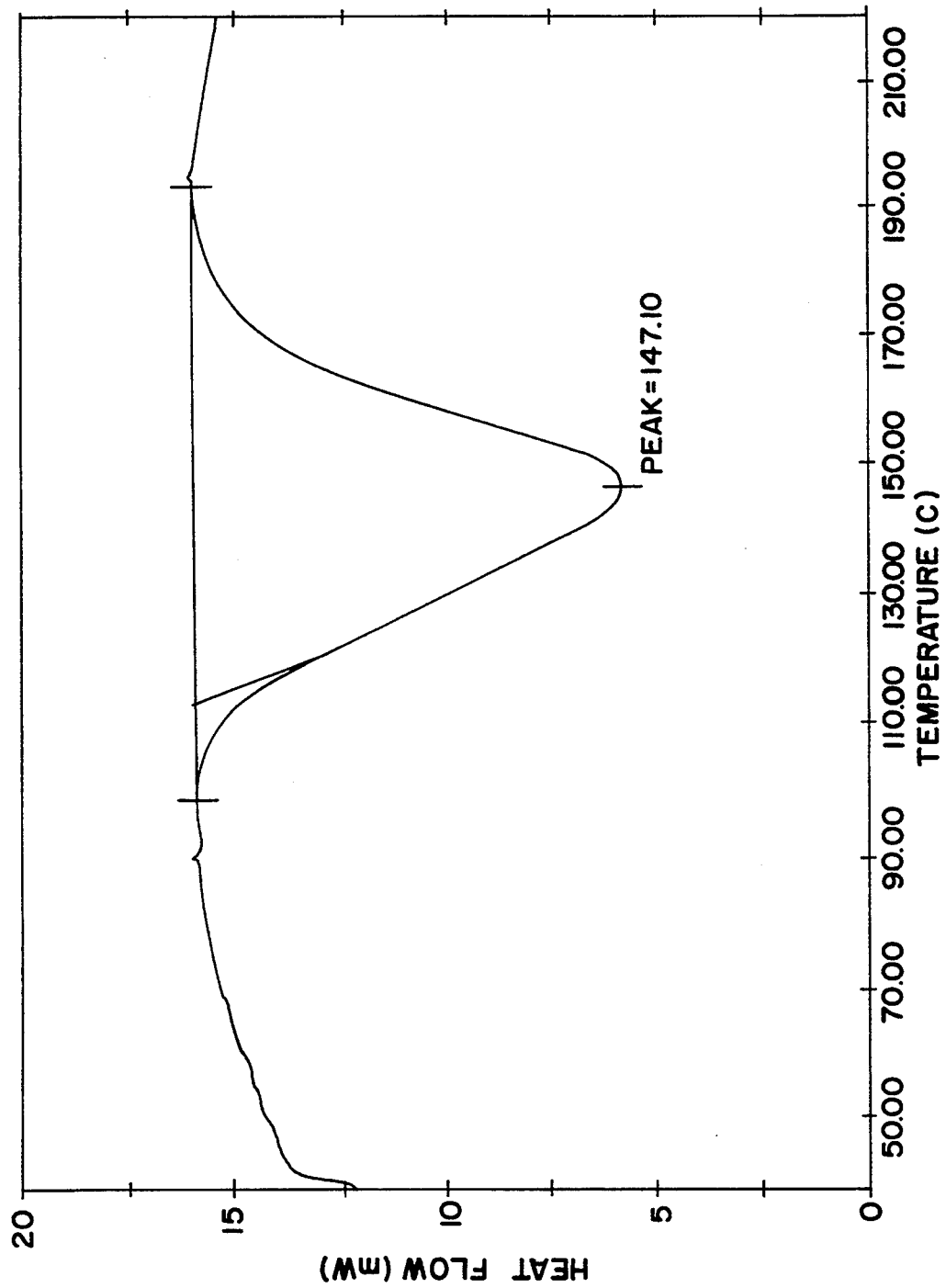
Figure 9:
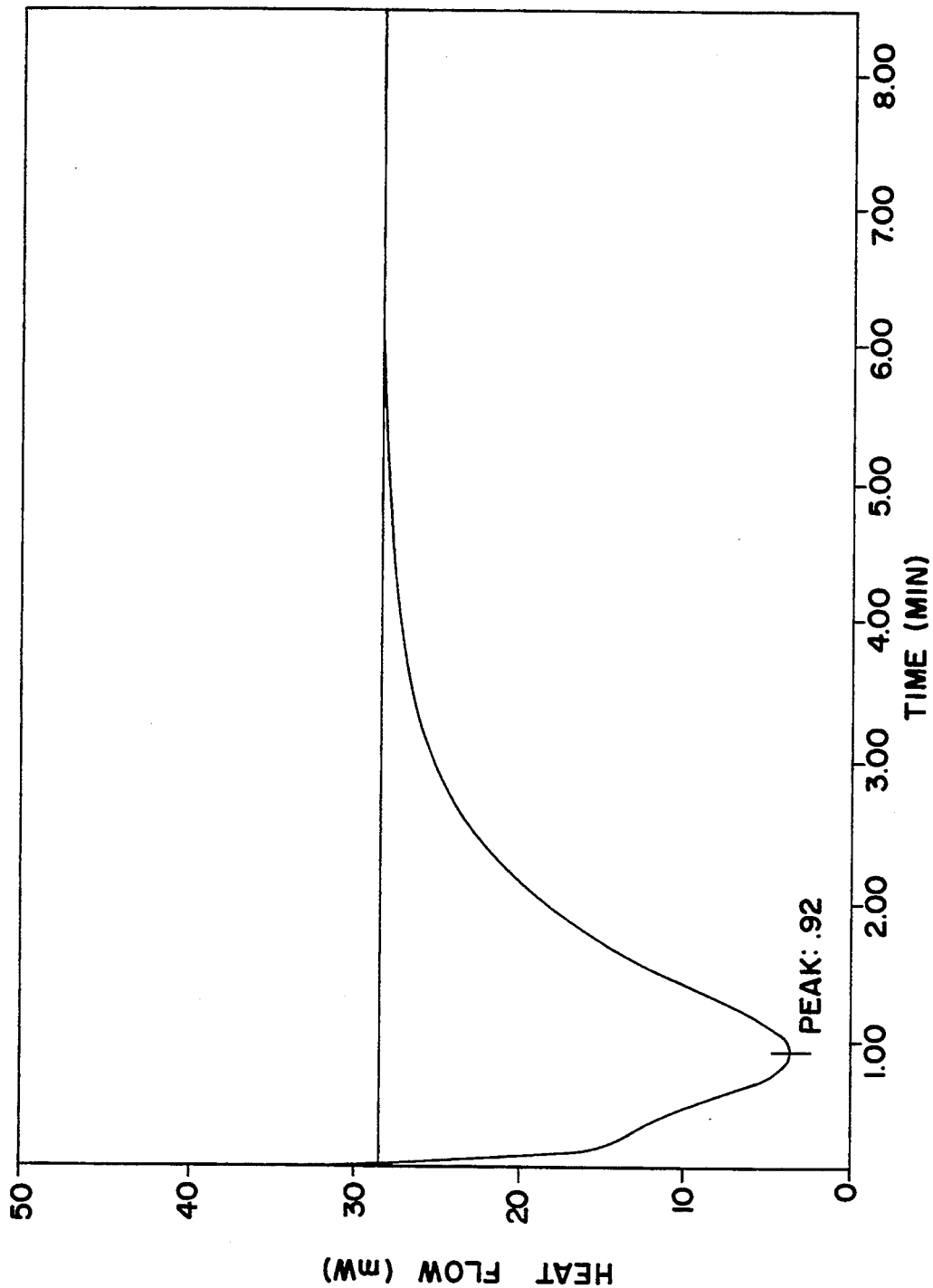

The complexes of example 9 to 11 were characterized by the IR spectra of FIGS. 1 to 3, respectively. Their suitability in catalytic curing was documented by differential scanning calorimetry (DSC). For this purpose, the catalyst was worked into a base resin (Rütapox 0164LV) in a mole ratio to 1:0.05 and first measured with dynamic DSC. To represent the high reactivity (short reaction time), curing was carried out at the peak maximum temperature in a repeated measurement. The corresponding dynamic and isothermic DSC diagrams are included with these examples as FIGS. 4 to 9.

Various modifications of the products and processes of the invention may be made without departing from the spirit or scope thereof and it is to be understood that the invention is intended to be limited only as defined in the appended claims.

What we claim is:

1. A process for the preparation of neutral metal complex salts of the formula $M^{a+}(SR^{b-})$ n—o $L_x$ $B_y$ wherein M is an ion of a metal selected from the group consisting of cobalt, nickel, iron, zinc, manganese, copper, mercury, zirconium, tin, cadium, titanium, vanadium, indium, silver, chromium and antimony, SR is an acid radical of an organic or inorganic acid, B is a Lewis base of the group consisting of pyridine or an imidazole and L is a chelating ligand, wherein a=an integer of 1-8,
b=an integer of 1-3,
n=an integer of 1-8,
o=an integer of 0-8,
x=an integer of 0-4, and
y=an integer of 8-15 wherein $(n-o)+x+y \leq 16$, characterized in that the metal salt, chelating ligand and Lewis base are mixed together in stoichiometric amounts in the absence of a solvent and reacted in a molten stage at a temperature of 20° to 200° C.

2. The process of claim 1 wherein the temperature is 25° to 150° C.

3. The process of claim 1 wherein the product is crystallized as a fine-grained powder by slowly cooling at high stirrer speeds.

4. The process of claim 3 wherein the powder is ground.

5. The process of claim 1 wherein the reaction mixture is sprayed to obtain the complex as a fine-grained powder.

6. The process of claim 1 wherein the chelating ligand is selected from the group consisting of dioximes, α- and β-hydroxycarbonyl compounds, ketones, aldehydes, and enolizable ketones.

7. The process of claim 1 wherein the chelating ligands are selected from the group consisting of hydroxycarboxylic acids, acetylacetone, benzoyl acetone, dipivaloylmethane and dimethly-glyoxime.

8. The process of claim 1 which is continuous.

9. A complex salt formed by the process of claim 1.

10. The process of claim 1 wherein M is selected from the group consisting of copper, iron and nickel, the Lewis base is pyridine and the chelating ligand is acetyl acetone or salicylaldehyde.

* * * * *